United States Patent [19]

Honda

[11] Patent Number: 4,918,713
[45] Date of Patent: Apr. 17, 1990

[54] SYSTEM AND METHOD FOR CORRECTING FOR SCATTERED X-RAYS

[75] Inventor: Michitaka Honda, Nishinasuno, Japan

[73] Assignee: Kabushiki Kaisha Toshiba, Kanagawa, Japan

[21] Appl. No.: 16,129

[22] Filed: Feb. 18, 1987

[30] Foreign Application Priority Data

Feb. 18, 1986 [JP] Japan .................................. 61-33553

[51] Int. Cl.⁴ .......................... G21K 1/00; H05G 1/64
[52] U.S. Cl. ........................................ 378/99; 378/7; 378/87; 358/111
[58] Field of Search ........................ 378/7, 99, 87, 154, 378/2, 149, 155, 204, 207, 901; 333/174; 364/414, 604; 358/284, 111

[56] References Cited

U.S. PATENT DOCUMENTS

| | | |
|---|---|---|
| 2,336,026 | 12/1943 | Millenaar . |
| 2,679,008 | 5/1953 | Hall . |
| 3,860,821 | 1/1975 | Barrett . |
| 4,081,681 | 3/1978 | Froggatt .................................. 378/7 |
| 4,087,837 | 5/1978 | Geluk . |
| 4,114,041 | 9/1978 | Oliver . |
| 4,286,156 | 8/1981 | Wagner . |
| 4,380,817 | 4/1983 | Harding et al. . |
| 4,380,818 | 4/1983 | Pfeiler . |
| 4,399,547 | 8/1983 | Riederer et al. . |
| 4,497,062 | 1/1985 | Mistretta ............................ 378/158 |
| 4,549,307 | 10/1985 | Macovski . |
| 4,550,419 | 10/1985 | Aichinger et al. . |
| 4,571,635 | 2/1986 | Mahmoodi et al. ................. 358/284 |
| 4,599,742 | 7/1986 | Kikuchi et al. ....................... 378/99 |
| 4,653,080 | 3/1987 | Kikuchi et al. ....................... 378/87 |
| 4,656,650 | 4/1987 | Kikuchi et al. . |
| 4,677,681 | 6/1987 | Klauz ..................................... 382/6 |
| 4,688,242 | 8/1987 | Ema ..................................... 378/154 |

FOREIGN PATENT DOCUMENTS

| | | |
|---|---|---|
| 0001523 | 4/1979 | European Pat. Off. . |
| 0037722 | 4/1981 | European Pat. Off. . |
| 0116941 | 2/1984 | European Pat. Off. . |
| 0105618 | 4/1984 | European Pat. Off. . |
| 0123276 | 10/1984 | European Pat. Off. . |
| 2452166 | 5/1976 | Fed. Rep. of Germany . |
| 2454537 | 5/1976 | Fed. Rep. of Germany . |
| 2459890 | 7/1976 | Fed. Rep. of Germany . |
| 3304213A1 | 8/1984 | Fed. Rep. of Germany . |
| 2526575 | 11/1983 | France . |

OTHER PUBLICATIONS

*Reference Data for Radio Engineers,* 4th Ed., International Telephone and Telegraph Co., 1956, pp. 1002–1003.

Primary Examiner—Carolyn E. Fields
Assistant Examiner—Joseph A. Hynds
Attorney, Agent, or Firm—Finnegan, Henderson, Farabow, Garrett and Dunner

[57] ABSTRACT

The radiation image in a radiation imaging system is improved by extracting a scatter distribution and subtracting the scatter distribution from the radiation image. The scatter distribution is extracted from the radiation image by an adaptive filter using a scatter-glare point spread function. The scatter-glare point spread function is obtained by measurements of the radiation system.

20 Claims, 15 Drawing Sheets

SYSTEM AND METHOD FOR CORRECTING FOR SCATTERED X-RAYS

BACKGROUND OF THE INVENTION

I. Field of the Invention

This invention relates generally to X-ray imaging systems and related methods, and more particularly this invention relates to a system and related method of compensating for scattered X-rays and veiling glare fraction degrading of image contrast and sharpness.

II. Background Information

X-ray imaging systems provide non-destructive or in vivo images of an object such as a patient. An X-ray source irradiates an X-ray beam towards the object. The X-ray beam is attenuated and scattered by the tissues or elements of the object. A radiation detector detects the attenuated and scattered X-ray beam and converts it into an electrical signal indicating an intensity of the detected beam. This electrical signal may be displayed as a visual image on a TV monitor. The scattered radiation impinges on the detectors from a path outside a direct path from the X-ray source to the detectors. This scattered radiation is added to a primary or non-scattered radiation through a direct path from the source to the detectors. Consequently, that portion of the resultant image due to the scattered radiation obscures that portion of the resultant image due to the non-scattered radiation. Furthermore, fluoroscopic systems make the resultant radiation image unclear due to optical scatter known as veiling glare.

Conventionally, there are two well-known techniques to minimize the effects of scattered radiation. The first of these techniques is disclosed in U.S. Pat. No. 4,549,307 issued to Macovski. The assignee of this application has also filed the following applications which generally relate to this first technique: U.S. application Ser. No. 601,349, filed Apr. 14, 1984 by Kikuchi; U.S. application Ser. No. 673,792, filed Nov. 21, 1984 by Kikuchi et al.; U.S. application Ser. No. 719,168 filed Apr. 2, 1985 by Kikuchi et al.; U.S. application Ser. No. 792,855 filed Oct. 30, 1985 by Yamagata et al., now U.S. Pat. No. 4,741,009, issued Apr. 26, 1988; and U.S. application Ser. No. 857,050, filed Apr. 29, 1986 by Ema now U.S. Pat. No. 4,688,242.

In this first technique, actual scattered radiation is measured using an X-ray opaque dot or dots. The resultant scattered X-ray image at the locations of these dots is used to estimate the scattered X-ray image throughout the entire image. A radiation image is then obtained without the X-ray opaque dot or dots. This radiation image is corrected using the estimated scattered X-ray image for the entire image.

Using this first technique, it is necessary to irradiate additional X-rays towards the object to estimate a scattered X-ray image. This increases the X-ray dose delivered to the object; i.e., a patient. Furthermore, the scattered image between the X-ray opaque dots is estimated by interpolation, therefore the resultant scattered X-ray image for the entire image is not precise.

A second technique is taught by U.S. Pat. No. 4,599,742 issued to Kikuchi et al. The assignee of this application has also filed U.S. application. Ser. No. 575,549 on Jan. 31, 1984, now U.S. Pat. No. 4,653,080, issued Mar. 24, 1987 by Kikuchi et al., which generally relates to this second technique.

In this second technique, an acquired radiation image T is represented as follows:

$$T = S + P \quad (1),$$

where S is a scatter-glare distribution and P is a primary or non-scatter distribution. This second technique depends on a theory that the scatter distribution S is approximated as follows:

$$S \approx cP^n ** PSF \quad (2)$$

(** denotes two dimensional convolution operation), where PSF is a scatter point spread function, and c and n are appropriate constants. Thus, this second technique teaches that the scatter distribution S is represented as a non-linear expression of the primary distribution P.

Furthermore, the equation (2) is approximated to solve the equation (1) practically as follows:

$$S \approx (aP + d) ** PSF \quad (3),$$

where a and d are appropriate constants defined so that a line represented by the equation (3) is tangent to a curve represented by the equation (2) at mean P in an P-S co-ordinate system.

Equation (1) is rewritten from equation (3) as follows:

$$T \approx aP  PSF + d  PSF + P \quad (4).$$

The primary distribution P is obtained by solving equation (4) after acquiring a radiation image from the detectors.

In this second technique, however, the primary distribution P is obtained by directly solving equation (4) for each pixel. Thus, each pixel of the primary distribution P is calculated one pixel by one pixel, for example $512 \times 512$ times when the size of the acquired image is $512 \times 512$ pixels. Accordingly, this second technique takes a long time to obtain the primary distribution P, i.e., a scatter-free image.

Furthermore, since the primary distribution P includes a high-frequency component, an error is introduced when the primary distribution P is calculated from the equation (4).

An objective of the present invention is to provide an improved system and method for correcting for scattered X-rays.

In the case of using an image intensifier (I.I.), the present invention provides a system and method for correcting not only for scattered X-rays, but also for veiling-glare generated by optical scatter fraction from output phosphor.

Another object of the present invention is to provide a system and method for enabling a rapid correcting for scattered X-rays and/or veiling glare fraction.

Another object of the present invention is to provide a system and method for diminishing solution error in solving for the primary distribution of an image.

SUMMARY OF THE INVENTION

A feature of the invention is to calculate the scatter distribution S by using adaptive filtering and then subtract the scatter distribution S from the acquired image T to obtain the primary distribution P. The scatter distribution S is a lower frequency distribution than the primary distribution. Accordingly, it is possible to diminish the size of the scatter distribution S from, for example, 512×512 pixels into 64×64 pixels, to enable 64 times as rapid calculation as that of 512×512 pixels. Since the scatter distribution S is a lower frequency distribution, it causes less error than the primary distribution in an inverse or iterative filter procedure in an X-Y domain or frequency domain.

Another feature of the present invention is to alter a grey scale of the acquired image before the inverse or iterative filter process, to diminish error.

Further, another feature is to give more accurate scatter distribution which includes a non-linear part of the primary distribution P and a linear part of P.

DETAILED DESCRIPTION OF THE PREFERRED EMBODIMENT

The present invention is based on the following three experimental facts:

I. First, the shape of a scatter-glare point spread function PSF for scattered radiation is dependent on irradiation conditions like X-ray tube voltage and the distance between an object and a grid for reducing the scattered radiation applied in front of an image area detector like an image intensifier (I.I.), but independent of the thickness of the object and the distance between the object and the image area detector.

Figure 1:
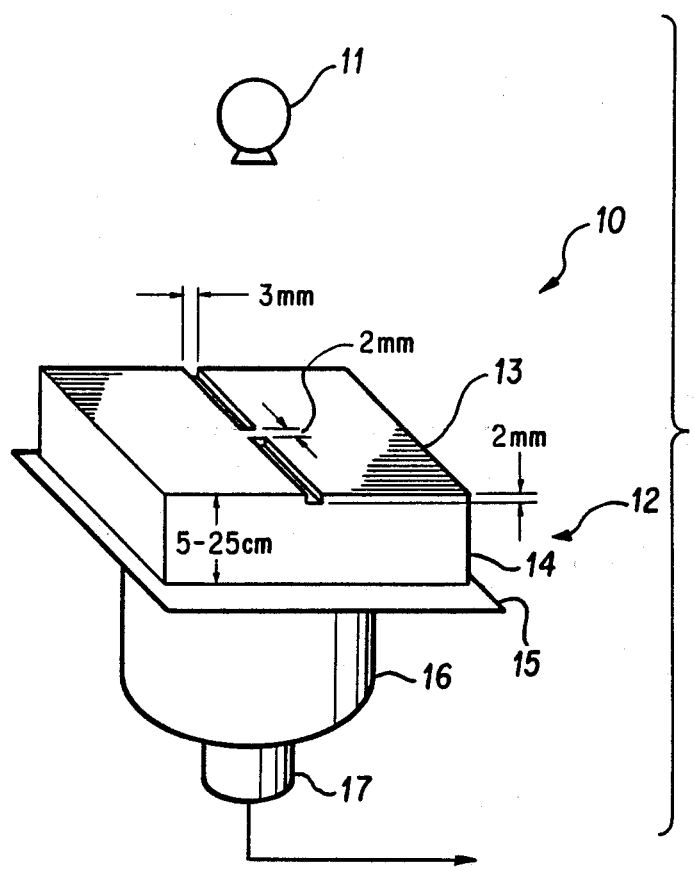
FIG. 1 illustrates a device for measuring the scatter glare point spread function of an X-ray apparatus using an imager intensifier.

In this regard, FIG. 1 shows a device 10 for measuring the scatter-glare point spread function of an X-ray apparatus or the like. An X-ray tube 11 irradiates X-ray radiation toward a phantom 12. Phantom 12 includes an H-shaped lead plate 13 2 mm thick and a water bag 14 which is variable between 5 to 25 cm thick. The H-shaped lead plate 13 has slits of 3 mm width bisecting it, with a remaining center portion of 2 mm width. X-ray radiation irradiated from X-ray tube 11 penetrates the 3 mm wide slits of the lead plate 13, but does not pass the other portions of plate 13. The water bag 14 makes the X-ray radiation penetrating the slits scatter. The scattered radiation from the water bag 14 is slightly reduced by a conventional grid 15. The scattered radiation passing through the grid 15 is detected by an image intensifier 16. The image intensifier 16 converts X-ray radiation impinged on it into photons and amplifies the same. A video camera 17 disposed at an output of the image intensifier 16 acquires a scatter-glare point spread function (PSF) along the X-axis. After obtaining this output for the X-axis, the phantom 12 is rotated by 90° and the same procedure is repeated to acquire another PSF along the Y-axis.

Thus the PSFs along the X and Y axis of device 10 may be acquired. A radiation image of an object is acquired by the device 10 by replacing the phantom 12 with the object.

Figure 2:
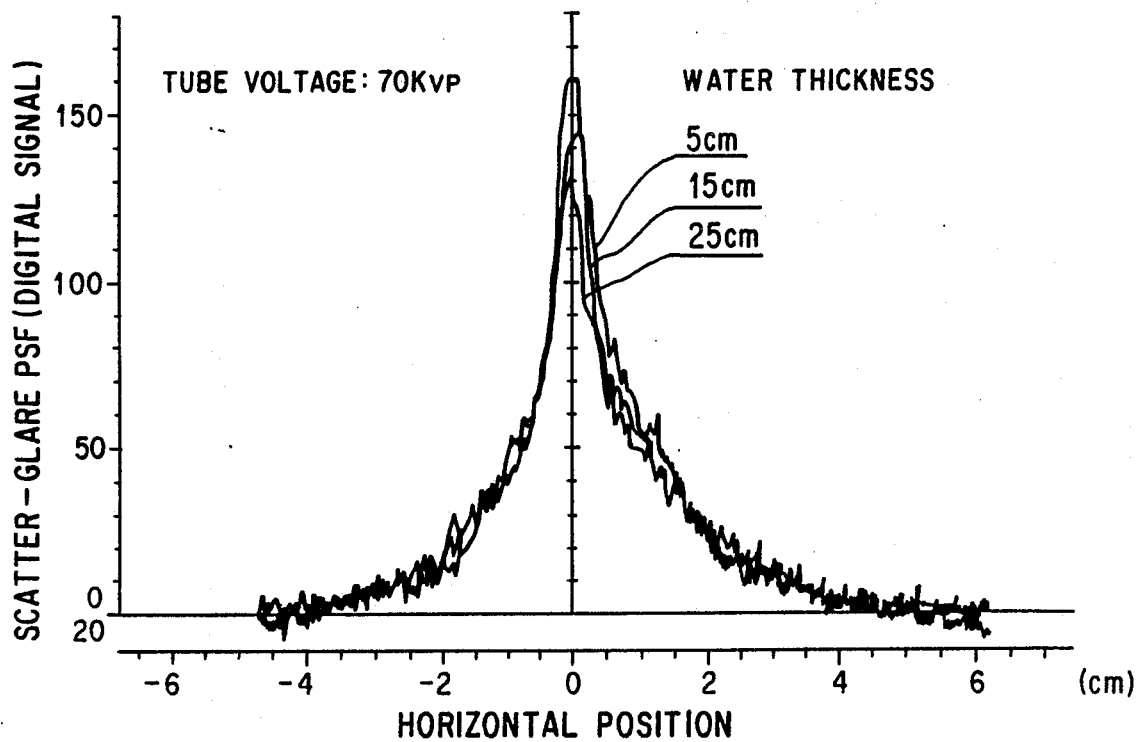
FIG. 2 illustrates measured scatter-glare point spread functions under different X-ray tube voltages by the device shown in FIG. 1.

FIG. 2 shows the PSFs which may actually be acquired by the device 10, by varying the thickness of the water bag 14 from 5 cm to 15 cm to 25 cm, using a tube voltage of 70 kvp. There is not a big difference between PSFs with different water bag thicknesses of 5 cm, 15 cm and 25 cm. Accordingly, the PSF is believed to be essentially independent of the thickness of the object.

Furthermore, the resultant PSF extends as widely as the image intensifier can detect radiation.

II. Second, a scatter quantity S is represented by $$S = (AP^n + BP) \quad (5),$$

where P is a primary quantity and A, n, B are constants estimated from irradiation conditions.

The constant n is around 0.95 within the typical tube voltage range of 60 kvp–130 kvp in the medical field.

The equation (5) may be rewritten in an experimental form as follows:

$$S = 4.3 \times \left( \text{tube current} \times \text{irradiation period} \times \left( \frac{100}{FDD} \right)^2 \times \text{diaphragm ratio} \right)^{0.16} \times P^{0.95} - 2.69 \times P \quad (6)$$

$$= 5.83 \times P^{0.95} - 2.69 P,$$

where the irradiation conditions are as follow:

| | |
|---|---|
| tube voltage | 116 kvp, |
| tube current | 60 mA, |
| irradiation time period | 33 mS (continuous X-ray), |
| iris ratio | 0.024, |
| FDD (= a distance between X-ray tube and a detector) | 100 cm, |
| phantom | water, |

| | -continued |
|---|---|
| grid | 40 lines per cm |
| height:pitch | 10:1 |
| spacer material | wood of 2 mm thick |
| parallel grid, and irradiation area | 23 cm × 23 cm (9 inch image intensifier) |

Figure 3:
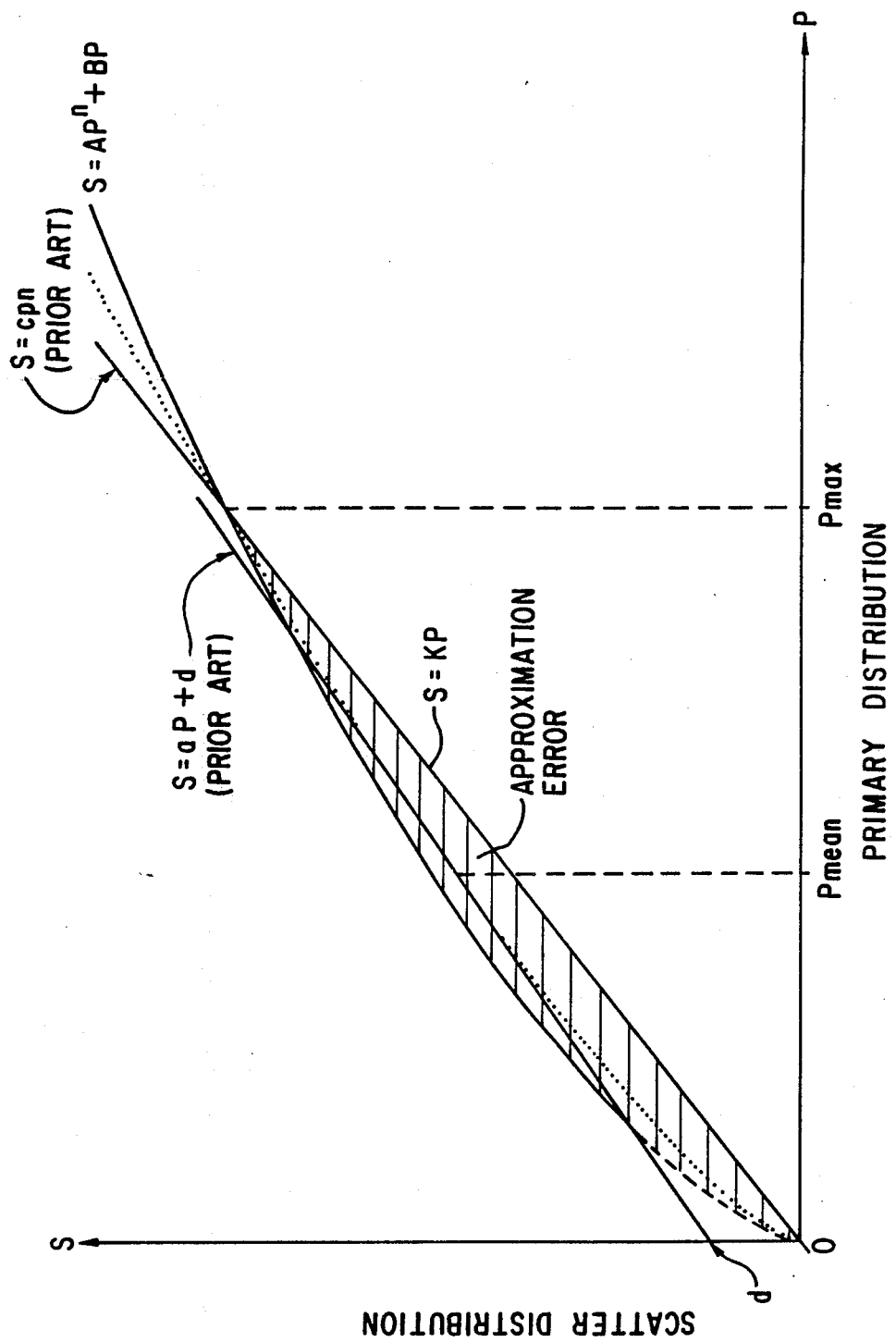
FIG. 3 illustrates the relation between a primary distribution P and a scatter distribution S in a P-S coordinate system and a linear approximation function of that relation.

FIG. 3 shows a relation between the primary quantity P and scatter quantity S in the P-S domain. Recent experiments indicate that S includes a linear portion B·P of P except for a non-linear portion $A·P^n$ of P. This linear portion becomes sensitive to portions near the circumference of the radiation image. Therefore, adding the B·P to S improves the scatter correction of those portions.

A scatter distribution S(x, y) is represented from the equation (5) as follows:

$$S(x, y) \simeq \iint_D \{A \cdot P^n(x - x', y - y') + B \cdot P(x - x', y - y')\} \times \widehat{PSF}(x', y')dx'dy', \quad (7)$$

where D indicates irradiation area and $\widehat{PSF}$ is a normalized PSF satisfying the following equation (8):

$$\int_\infty^\infty \int_\infty^\infty \widehat{PSF}(x', y')dx'dy' = 1 \quad (8)$$

$$= \iint_D \widehat{PSF}(x', y')dx'dy' = 1.$$

Since n is nearly 1, i.e., 0.95 in the medical field, $p^n(x, y)$ will be converted into a Taylor series at Pmean. At that time, S(x, y) includes a constant portion as well as a portion proportional to P. This constant portion not only increases the amount of time required to obtain a solution, but also makes hardware or software necessary to obtain a solution.

Therefore, in a favorable system and method, $P^n(x, y)$ is approximated as follows:

$$P^n(x, y) \simeq K \cdot P(x, y) \quad (9),$$

where K is a constant.

The constant K is approximately obtained from the maximum grey level Tmax in the acquired image T as follows:

$$K = Tmax^{n-1} \quad (10).$$

But, the constant K does not need to be obtained with strict accuracy.

Therefore, S(x, y) is rewritten from the equation (9) as follows:

$$S(x, y) = (A + K \cdot B) \cdot \iint_D P(x - x', y - y') \cdot \widehat{PSF}(x', y')dx'dy'. \quad (11)$$

III. Third, the acquired image T(x, y) is described as a summation of S(x, y) and P(x, y) as follows:

$$\begin{aligned} T(x, y) &= S(x, y) + P(x, y) \quad (12) \\ &= (AK + B) \cdot \iint_D P(x - x', y - y') \cdot \\ &\quad \widehat{PSF}(x', y')dx'dy' + P(x, y). \end{aligned}$$

For a simple expression, the equation (12) is rewritten as follows:

$$T = C \cdot P ** \widehat{PSF} + P \quad (13)$$

where C=AK+B.

In the preferred system and method, grey scales of T are altered into T' to lessen the approximation error of equation (9) as shown in FIG. 3 prior to solving equation (13) as follows:

$$T' = \rho1 T^{\rho2} \quad (14),$$

where ρ1, ρ2 are constants.

The constants ρ1, ρ2 are obtained as follows: If the irradiated field is large enough and the object is uniform, the equation (13) will be rewritten as follows:

$$T = C \cdot P + P \quad (15).$$

The scattered portion is represented as $$\frac{c}{c+1} T$$

from the equation (15). The scattered portion C·P must also be equal to $AP^n + BP$ from equation (5). Therefore, $$\begin{cases} T = AP^n + BP + P, & (16a) \\ T' = (A \cdot P^n + BP) \frac{C+1}{C}. & (16b) \end{cases}$$

Values A, B, C and n are known constants and P is a caluclable parameter. Depending on the value of P, T and T' can be calculated from equations (16a) and (16b). For example, if independent cases wherein P=100 and P=1000 are assumed, values for $T_{P=100} T'_{P=100} T_{P=1000}$ and $T'_{P=1000}$ may be calculated. These values may be used in equation (14) to solve for the constants ρ1, ρ2.

Thus, the grey scale of the acquired image T is altered as shown by equation (14). Therefore the equation (13) is rewritten as follows:

$$T' = C \cdot P ** \widehat{PSF} + P \quad (17).$$

Equation (17) is solved to extract $P**\widehat{PSF}$ in both the X-Y and frequency domains according to the present invention.

In the X-Y domain, iterative filtration is preferable to extract $P**\widehat{PSF}$ from equation (17). $\widehat{PSF}$ has a function of a strong low pass filter.

By multiplying both sides of equation (17) by $\widehat{PSF}$, the following equation is obtained:

$$T'  \widehat{PSF} = C \cdot P  \widehat{PSF}  \widehat{PSF} + P  \widehat{PSF}(18-1),$$ where
$T'**\widehat{PSF}$ represents a first order filtering image.
Repeating multiplication of $\widehat{PSF}$, second order, third order, ..., kth order, ..., Nth order filtering images are obtained as follows:

$$T^{} \widehat{(PSF)}^2 = C \cdot P^{} \widehat{(PSF)}^3 + P^{**} \widehat{(PSF)}^2, \quad (18\text{-}2)$$
$$T^{} \widehat{(PSF)}^3 = C \cdot P^{} \widehat{(PSF)}^4 + P^{**} \widehat{(PSF)}^3, \quad (18\text{-}3)$$

$$T^{} \widehat{(PSF)}^k = C \cdot P^{} \widehat{(PSF)}^{k+1} + P^{**} \widehat{(PSF)}^k, \quad (18\text{-}k)$$

$$T^{} \widehat{(PSF)}^N = C \cdot P^{} \widehat{(PSF)}^{N+1} + P^{**} \widehat{(PSF)}^N. \quad (18\text{-}N)$$

The term $(PSF)^k$ means K times convolution of PSF as a filter.

Since $\widehat{PSF}$ has a function of a strong low pass filter and $P^{**}\widehat{PSF}$ is a scatter distribution of low frequency, the following relation is obtained:

$$P^{}\widehat{(PSF)}^{N+1} \approx P^{}\widehat{(PSF)}^N \quad (19),$$

if N is larger than a certain value.

Substituting the equation (18−N) by the equation (19), the equation (18−N) is rewritten as follows:

$$T^{}\widehat{(PSF)}^N = (C+1)P^{}\widehat{(PSF)}^N \quad (20).$$

Therefore, $$P^{} \widehat{(PSF)}^N = \frac{1}{C+1} \cdot T^{} \widehat{(PSF)}^N. \quad (21\text{-}N)$$

Substituting the equation (18−(N−1)) by the equation (21−N) the equation (18−(N−1)) is rewritten as follows:

$$P^{} \widehat{(PSF)}^{N-1} = T^{} \widehat{(PSF)}^{N-1} - \quad (21\text{-}N\text{-}1)$$
$$\frac{1}{C+1} T^{**} \widehat{(PSF)}^{N-1}.$$

By repeating this process, $P^{**}(PSF)$ is obtained as follows:

$$P^{}\widehat{(PSF)} = T^{}\widehat{(PSF)} - CT^{**} \widehat{(PSF)}^2 + \quad (22)$$
$$C^2 T^{} \widehat{(PSF)}^3 - C^3 T^{} \widehat{(PSF)}^4 + \ldots +$$
$$(-1)^{k-1} C^{k-1} {}^{**} \widehat{(PSF)}^k + \ldots +$$
$$(-1)^{k-1} C^{k-1} {}^{**} \widehat{(PSF)}^k + \ldots +$$
$$(-1)^{N-1} \frac{C}{C+1}^{N-1} T^{**} \widehat{(PSF)}^N.$$

Thus, the scatter distribution $P^{**}\widehat{(PSF)}$ is obtained.

Therefore the primary distribution P is obtained from the equation (13) as follows:

$$P = T - C \cdot P^{**}\widehat{(PSF)} \quad (23),$$

where T is the acquired image prior to grey scale alteration. Thus, P is obtained in the X-Y domain using iterative filtering.

The $P^{**}\widehat{(PSF)}$ term may also be extracted from the equation (17) in the frequency domain according to the present invention. Fourier transforming both sides of the equation (17), the equation (17) is rewritten as follows:

$$T(\omega) = C \cdot P(\omega) \cdot PSF(\omega) + P(\omega) = P(\omega)\{C \cdot PSF(\omega) + 1\} \quad (24),$$

where $T(\omega)$, $P(\omega)$ and $PSF(\omega)$ indicate Fourier transformations of respective T, P and $\widehat{PSF}$ and $\omega$ is a two dimensional vector in the equation (24).

This equation (24) is transformed as follows:

$$I(\omega) \cdot \frac{C \cdot PSF(\omega)}{1 + c \cdot PSF(\omega)} = CP(\omega) \cdot PSF(\omega) \quad (25)$$

by multiplying both sides of equation (23) by $$C \cdot PSF(\omega)/\{(1 + C \cdot PSF(\omega))\}. \quad (25 \text{ insert}).$$

Therefore, the scatter distribution $P(\omega) \cdot PSF(\omega)$ may be written:

$$P(\omega) \cdot PSF(\omega) = F(\omega)T(\omega)/C \quad (26),$$

where $$F(\omega) = C \cdot PSF(\omega)/(1 + C \cdot PSF(\omega)) \quad (26 \text{ insert}).$$

Inverse Fourier filtering both sides of equation (26), the equation (26) is rewritten as follows:

$$P^{}\widehat{PSF} = T^{}F/C \quad (27).$$

The convolution of $T^{**}F$ maybe performed in the X-Y domain as well as in the frequency domain.

By substituting equation (27) into equation (23), the primary P is obtained.

In the preferred method, the grey scale altered T' is minified in size and the minified T' is used in the process of the extraction of $P^{}\widehat{PSF}$ from equation (23) to lessen the quantity of calculation required. Then, the minified $P^{}\widehat{PSF}$ is magnified in size when $P^{**}PSF$ is subtracted from T.

Figure 4:
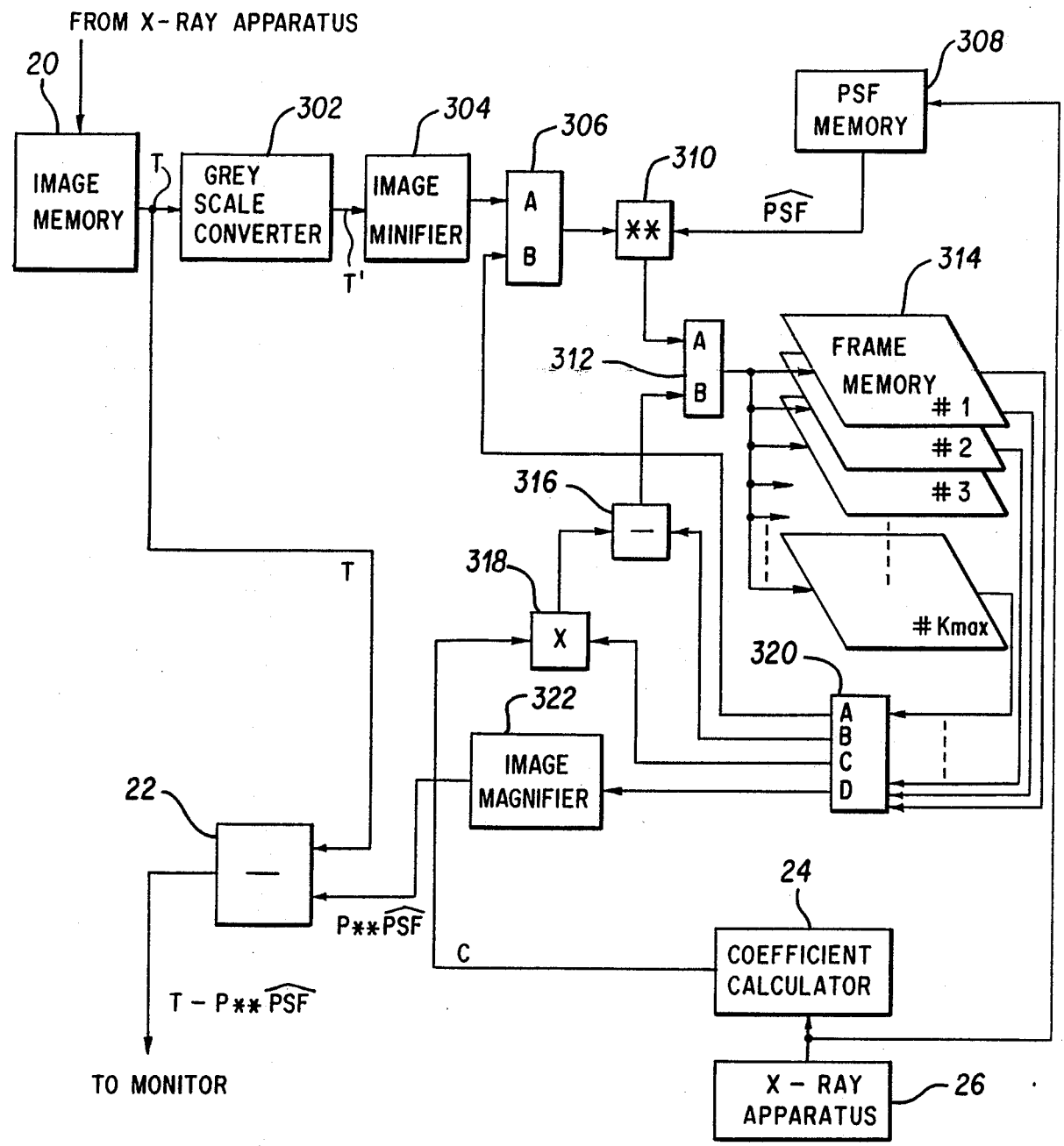
FIG. 4 illustrates a block diagram of a first embodiment of a system which incorporates the teachings of the present invention.

FIG. 4 shows a block diagram of a first embodiment according to the present invention. This embodiment obtains the primary distribution P from the acquired image T using an iterative filter in the X-Y domain.

The acquired image T of the size $512 \times 512$ pixels is provided from an X-ray apparatus and is stored in an image memory 20. The image memory 20 provides the image T to a grey scale converter 302 and a subtracter 22. The grey scale converter 302 alters the grey scale of the image T according to the equation (14) and produces the altered image T' to an image minifier 304. The image minifier 304 converts the image T' from $512 \times 512$ pixels into $64 \times 64$ pixels by averaging each $8 \times 8$ pixels and provides the minified output to a first selector 306. The selector 306 selects one among the outputs of the image minifier 304 and a second selector 320 and provides this selected output to a convolver 310.

Convolver 310 operates a convolution of the image T' and $\widehat{PSF}$ stored in a $\widehat{PSF}$ memory 308 and supplies the resultant convoluted image to a third selector 312. The $\widehat{PSF}$ memory 308 provides $\widehat{PSF}$ corresponding to the irradiation conditions of X-ray apparatus 26. Specifically, $\widehat{PSF}$ memory 308 stores $\widehat{PSF}$s actually acquired using a phantom 12 for various X-ray tube voltages prior to examination of an object, and stores one $\widehat{PSF}$ in accordance with the irradiation condition of X-ray apparatus 26. This $\widehat{PSF}$ depends on the X-ray tube voltage, i.e., the quality of the X-ray, but does not depend on the thickness of the object being examined. The selector 312 selects one among the outputs of convolver 310 and a first subtracter 316, and provides this selected output to one of frame memories 312 #1, ..., #kmax. The frame memories 312 #1, ..., #kmax store convoluted images and provide these images to a third selector 320. The selector 320 provides the convoluted image read from the frame memories 314 to the selector 306, the subtracter 316, a multiplier 318 and an image magnifier 322. The subtracter 316 subtracts the output of the selector 320 from the output of the multiplier 318. The multiplier 318 multiplies the output of the selector 320 by a coefficient C provided from a coefficient calculator 24. The coefficient calculator 24 provides the coefficient C according to the irradiation conditions of X-ray apparatus 26. Specifically, the coefficient C is defined in equation 13 as $C=AK+B$. A is defined from equation 6 as $4.3\times\{$ tube current $\times$irradiation time period $\times(100/FDD)\times$diaphragm ratio$\}$. B is defined from equation 6 as 2.69. K is defined in equation 10 with $\eta=0.95$. Thus, C depends on the tube current, irradiation time period, FDD, diaphragm ratio, and $T_{max}$ from the X-ray apparatus to calculate coefficient C from equation 13.

The image magnifier 322 converts the scatter distribution $P\widehat{PSF}$ from $64\times 64$ pixels into $512\times 512$ pixels by a technique such as a linear interpolation and provides the enlarged scatter distribution to a second subtracter 22. The subtracter 22 subtracts $P\widehat{PSF}$ from T provided from the image memory 20 and provides the result to a monitor (not shown).

Figure 5:
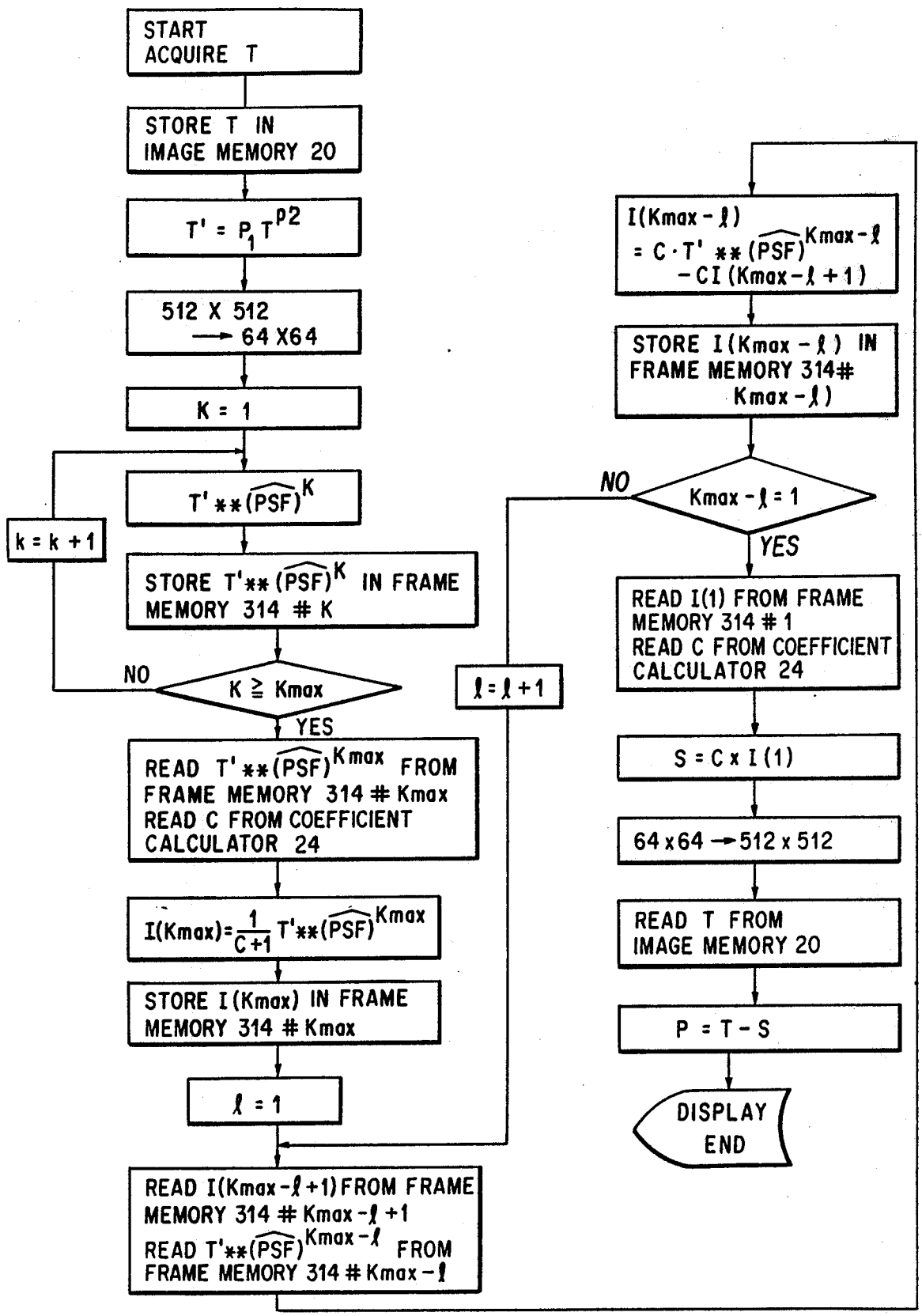
FIG. 5 illustrates a flow chart of operations of the first embodiment as shown in FIG. 4.
Figure 6:
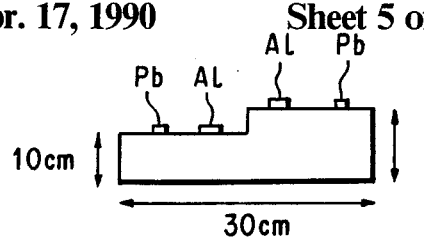
FIG. 6 illustrates a test phantom for acquiring an image including a primary distribution and a scatter distribution.
Figure 7:
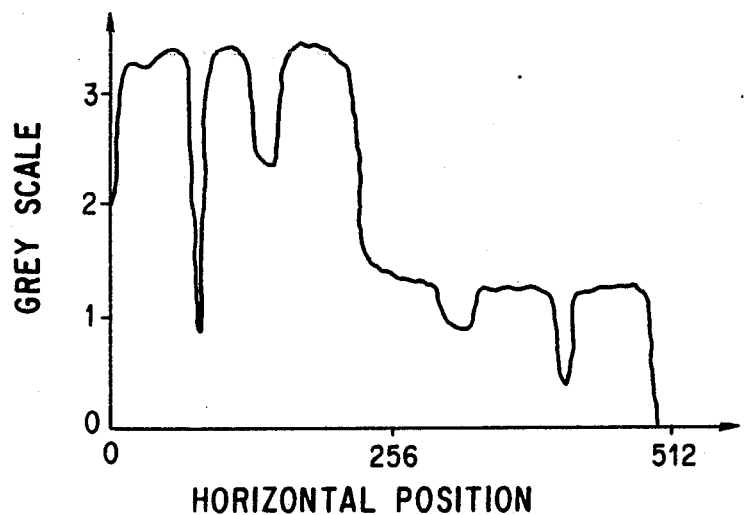
FIG. 7 illustrates a one dimensional acquired image of the test phantom as shown in FIG. 6.
Figure 8:
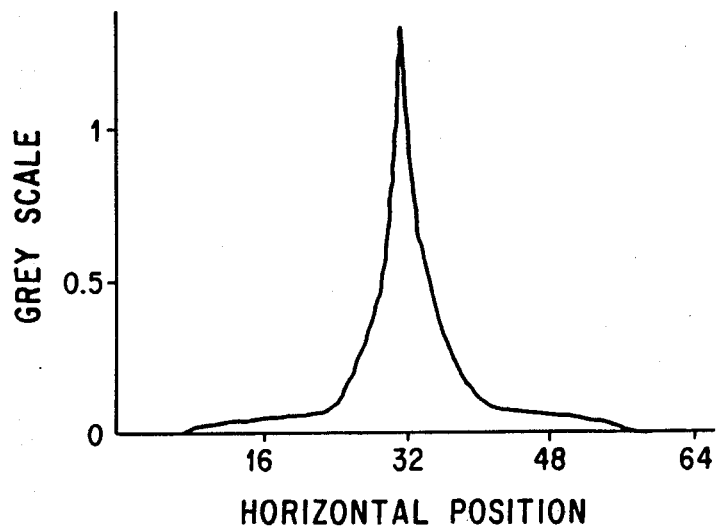
FIG. 8 illustrates a normalized scatter-glare point spread function.
Figure 9A:
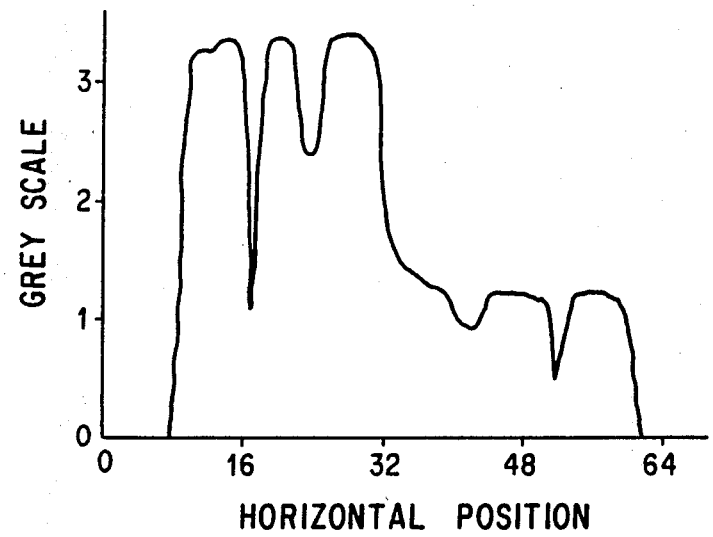
FIGS. 9A-9F and FIGS. 10A-10E illustrate respective convoluted images of the one dimensional acquired image as shown in FIG. 5 at each stage of an iterative filtering process operated by the first embodiment according to the present invention.
Figure 9B:
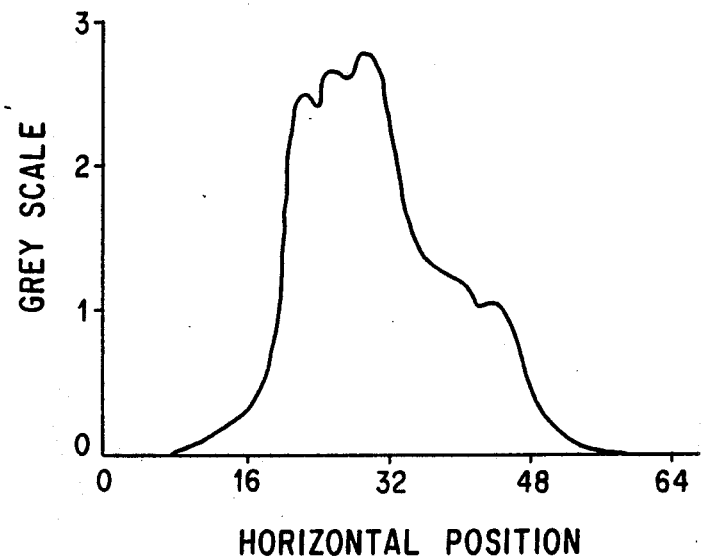
Figure 9C:
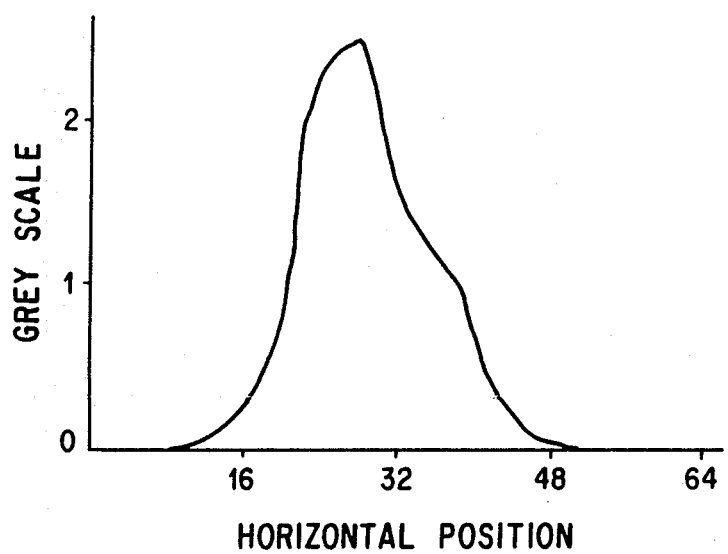
Figure 9D:
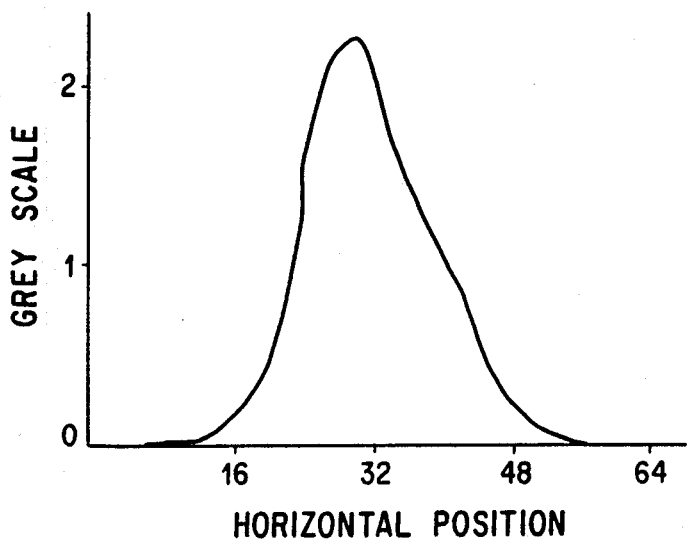

The operation of the embodiment described in FIG. 4 will be explained referring to a flow chart as shown in FIG. 5. The X-ray apparatus as shown in FIG. 1 irradiates X-ray radiation towards a phantom as shown in FIG. 6 and produces an X-ray image T as shown in FIG. 7. This X-ray image T consists of the scatter distribution S and the primary distribution P. This image T is converted into a digital form of $512\times 512$ pixels and is stored into the image memory 20. The grey scale of the image T is altered into T' according to the equation (14) by the grey scale converter 302. The size of this image is minified from $512\times 512$ pixels into $64\times 64$ pixels by the image minifier 304. This minified image T as shown in FIG. 9A is convoluted with a convolution kernel, i.e., normalized $\widehat{PSF}$ read from the PSF memory 308 by the convolver 310 and provides $T'\widehat{PSF}$ as shown in FIG. 9B to the frame memory 314 #1 through the selector 312. The image $T'\widehat{PSF}$ read from the memory 314 #1 is convolved again by the convolver 310. The image $T'(\widehat{PSF})^2$ as shown in FIG. 9C is stored in the memory 314 #2. This convolution is repeated and $T'(\widehat{PSF})^3$, $T'(\widehat{PSF})^4$ and $T'(\widehat{PSF})^5$ as shown in FIGS. 9D, 9E and 9F are stored in the respective memories 314 #3, #4 and #5.

Figure 9E:
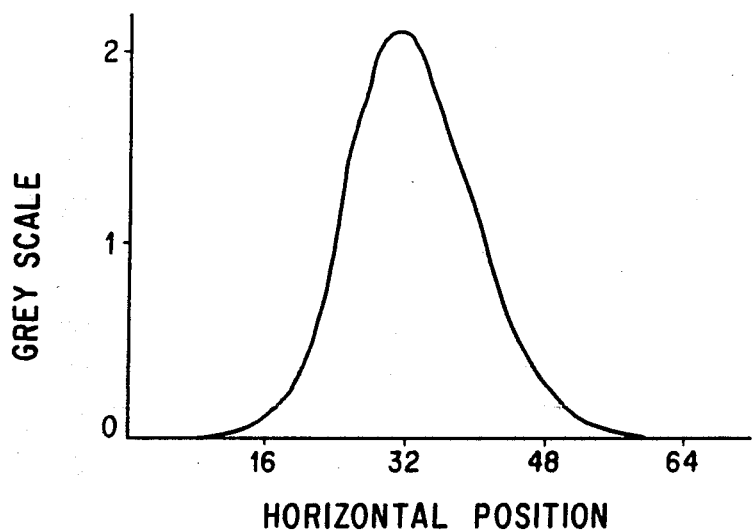
Figure 9F:
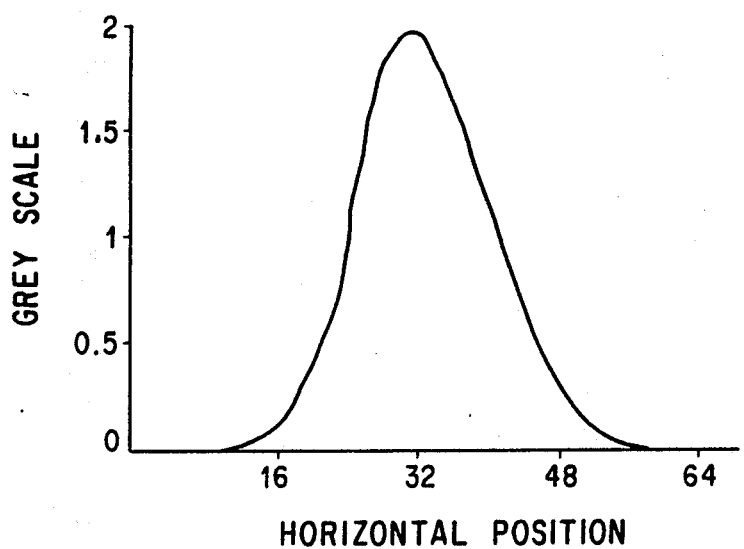

Since the convolution by $\widehat{PSF}$ is a strong low pass filter, the image $T'(\widehat{PSF})^4$ is similar to the image $T'(\widehat{PSF})^5$ as shown in FIGS. 9E and 9F. Therefore in this case, Kmax may be 5.

Figure 10A:
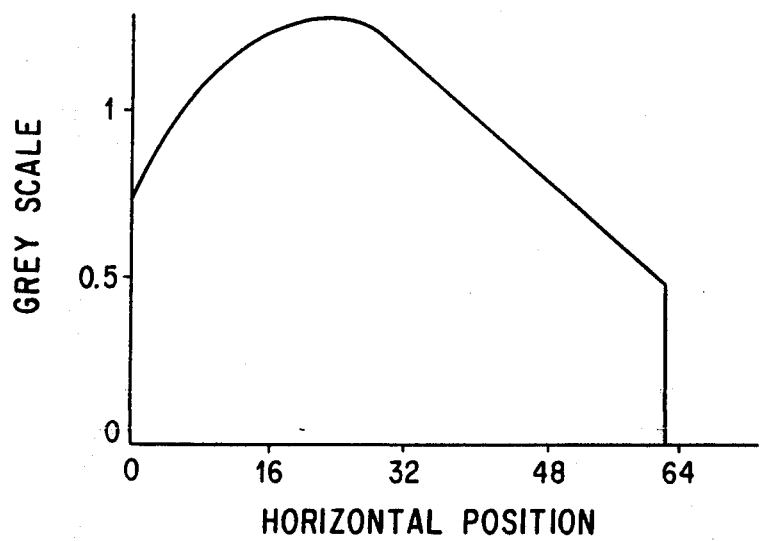
Figure 10B:
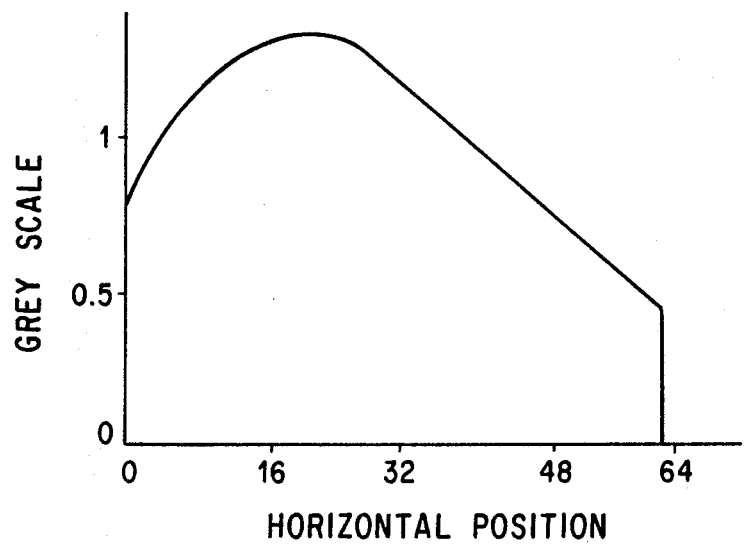
Figure 10C:
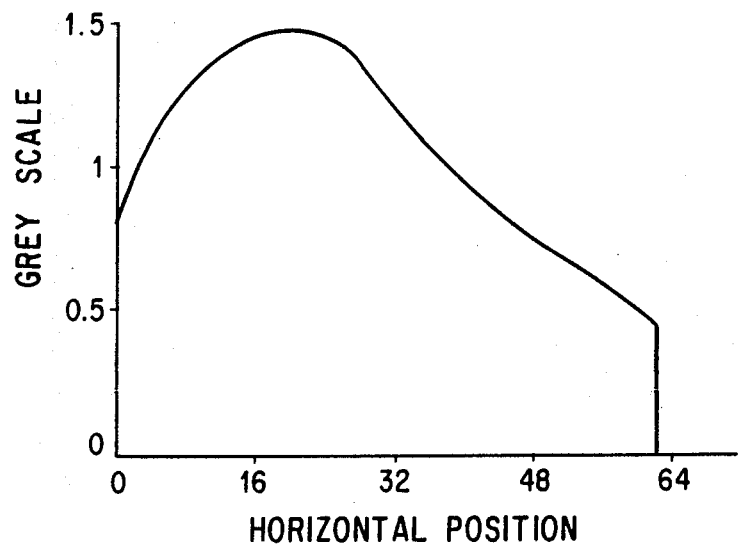
Figure 10D:
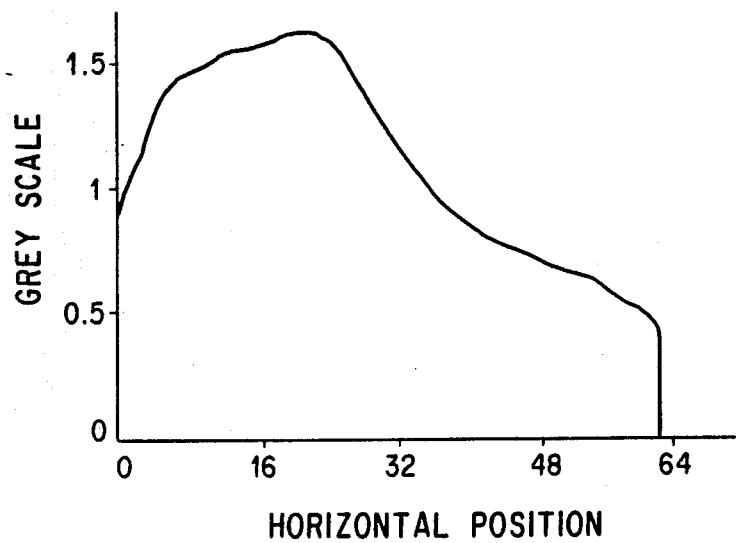
Figure 10E:
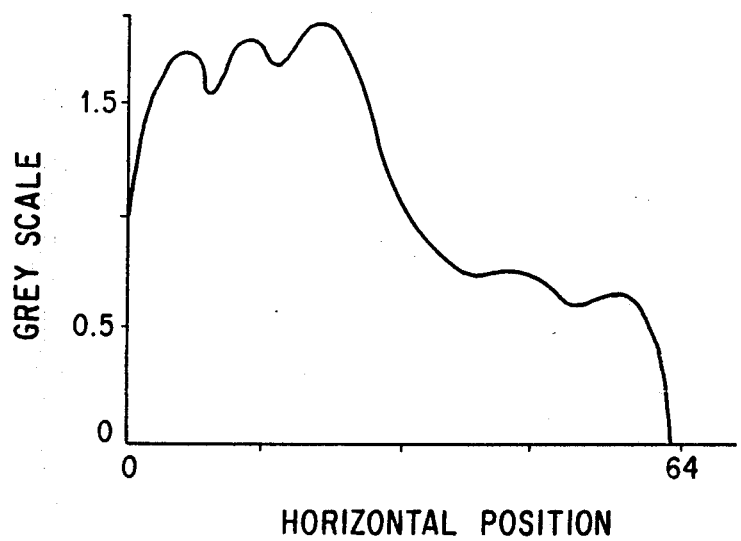
Figure 11:
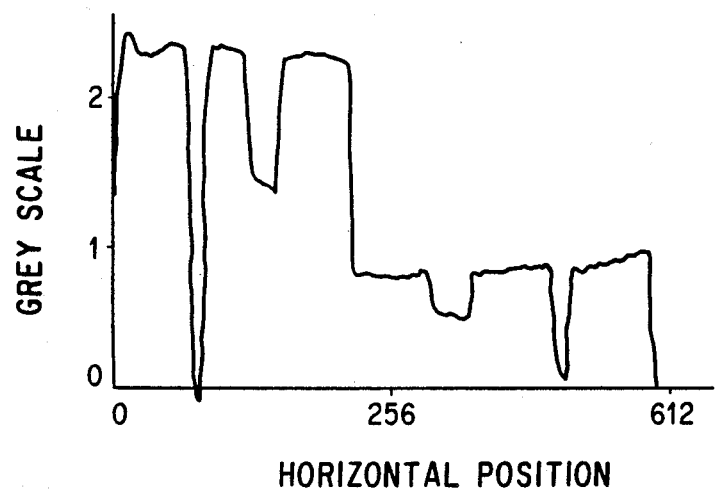
FIG. 11 illustrates a scatter-glare-free image of the test phantom as processed by the first embodiment of the present invention shown in FIG. 4.

After that, $T'(\widehat{PSF})^5$ is read from the memory 314 #5 and multiplied by $1/(C+1)$ by the multiplier 318. This $1/(C+1) T' (\widehat{PSF})^5$ as shown in FIG. 10A is restored in the frame memory 314 #5 through the selector 312. The coefficient $1/(C+1)$ is read from the memory 24. For simplification this image stored in the frame memory 314 #5 is indicated below as I(5). Next, the image I(5) stored in the frame memory 314 #5 is multiplied by C by the multiplier 318 and then subtracted from the image $T'(\widehat{PSF})^4$ stored in the memory 314 #4 by the subtracter 316. Thus $T' (\widehat{PSF})^4-I(5)$ as shown in FIG. 10B is restored into the memory 314 #4 through the selector 312. Hereafter $T'(\widehat{PSF})^4-I(5)$ is indicated as I(4). In a similar manner, $T'(\widehat{PSF})^{l-1}-C\cdot I(l)$ as shown in FIGS. 10C, 10D, and 10E and is calculated and restored in the memory 314 #1-1.

This calculation is repeated until $l=1$. Then I(1) (as shown in FIG. 10E), stored in the memory 314 #1 is read and provided to the image magnifier 322. The image I(1) is magnified from $64\times 64$ to $512\times 512$ by the image magnifier 322. This image I(1) is the scatter distribution $P**(\widehat{PSF})$ or S.

Figure 12:
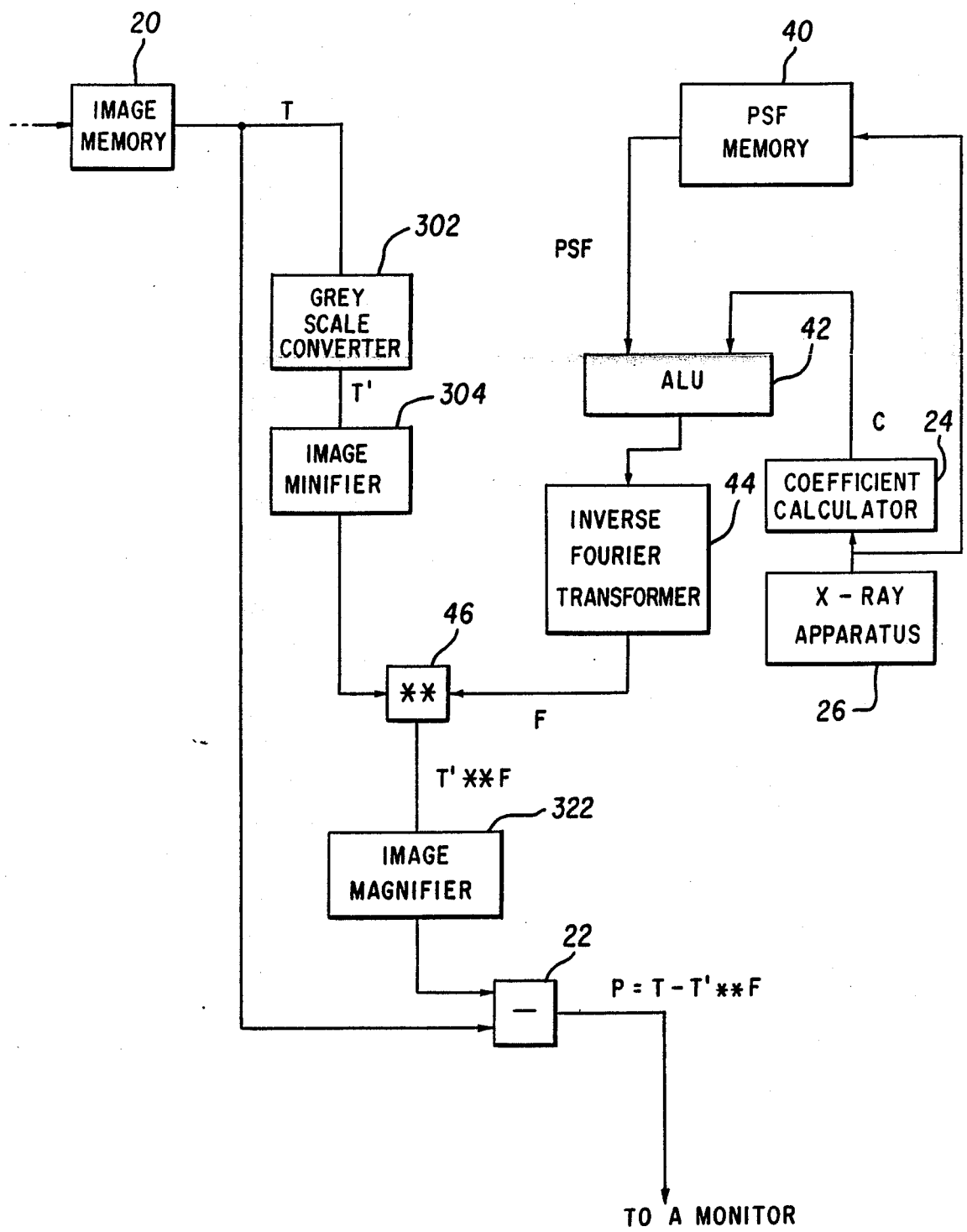
FIG. 12 illustrates a block diagram of a second embodiment of a system which incorporates the teachings of the present invention.

This scatter distribution S is subtracted from T stored in the memory 20 to produce a scatter-free image P or $T-P**\widehat{PSF}$ as shown in FIG. 12. The scatter-free image P is displayed on a monitor (not shown) in visual form or recorded in an X-ray film, or the like.

The minified size of the radiation image is preferably around one-eighth of the original because of the spectrum of the scatter distribution.

TOSHIBA Digital Fluorography System Model DFP-50A is used for digital image acquisition and processing for X-ray diagrams. This system may be modified by software application to practice the teachings of the subject invention and thereby obtain a scatter-glare-free radiation image in about 20 seconds. In a DFP-50A programmed according to the invention, the grey scale alteration and the image minifying and magnifying is performed by using software controlled hardware.

The following software applications may be added to the DFP-50A to practice of the invention:

1. A control to use the iterative filtering indicated by equations 18—1 to 22;

2. A function to estimate the scattered primary ratio by using the irradiated conditions indicated by equation 6;

3. A function to store the measured response function of a scattered radiograph and to normalize the same to the scattered $\widehat{PSF}$;

4. A function of subtraction between an acquired image and the estimated scatter image indicated by equation 23; and 5. A function to determine the grey scale application indicated by equations 14 to 16.

Figure 15:
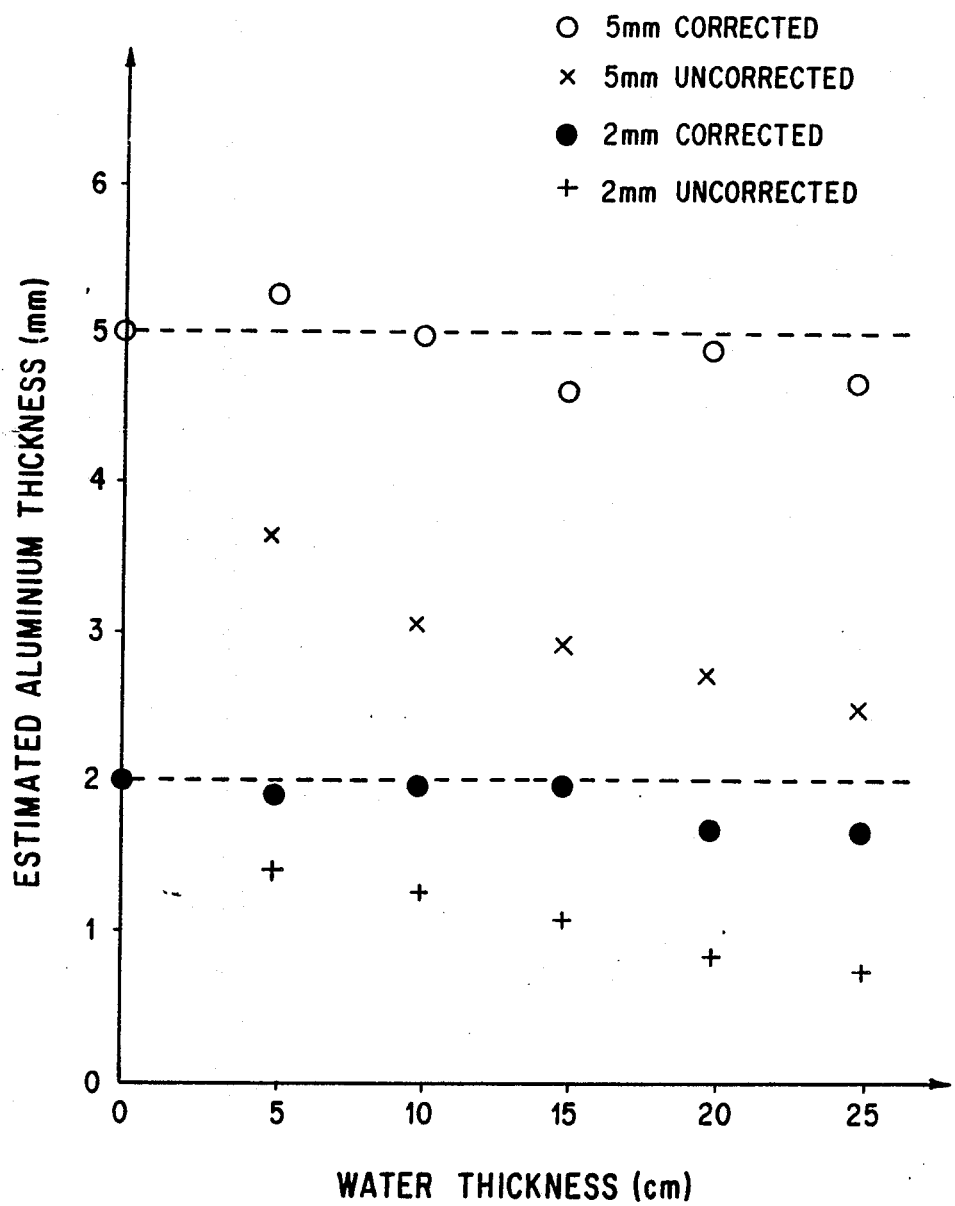
FIG. 15 illustrates experimental results showing the relationship between aluminum thickness estimated from corrected and uncorrected images and water thickness estimated from corrected and uncorrected images.

FIG. 15 shows a relationship between the thickness of an aluminum bar estimated from corrected and uncorrected images according to the applied DFP-50A and shows the water thickness, corrected and uncorrected, beneath the aluminum bar. The thicker the water is, the thinner the estimated aluminum bar thickness is, when the image is not corrected. But, the corrected image provides a more accurate estimated thickness than the uncorrected image. Thus, the present invention can improve the constant resolution of the image remarkably.

Figure 13A:
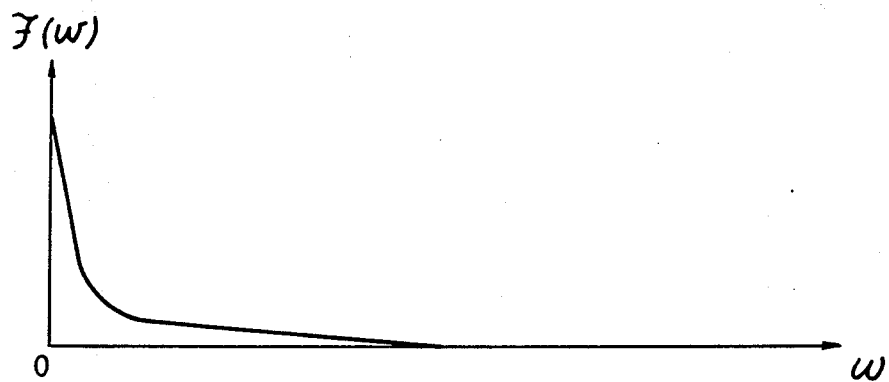
FIGS. 13 A and B illustrate a filter coefficient F(w) in a frequency domain and the same filter coefficient f(x, y) in an x-y domain.
Figure 13B:
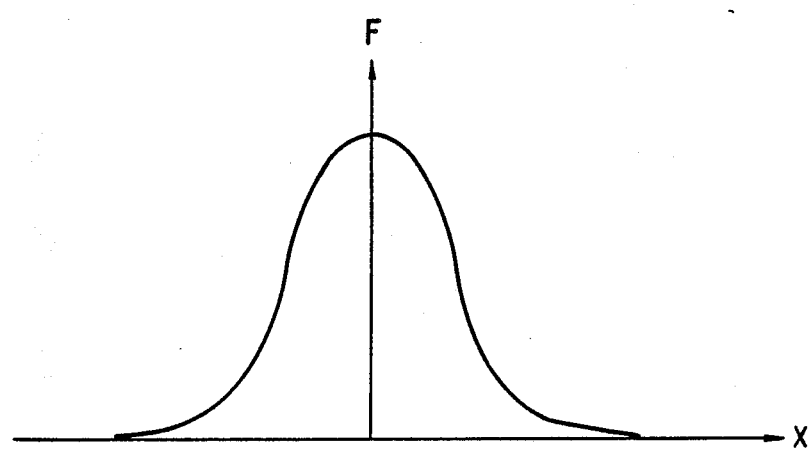

FIG. 12 shows a block diagram of a second embodiment according to the present invention which extracts the scatter distribution S from the acquired image T in a frequency domain. The image memory 20 stores the acquired image T and provides it to the grey scale converter 302 and to a subtracter 22. The grey scale converter alters the grey scale of the image T into T'. The image minifier 304 minifies the size of the image T' from $512\times 512$ pixels into $64\times 64$ pixels. The minified image T' is provided to a convolver 46. An X-ray apparatus 26 provides irradiation conditions to the coefficient calculator 24 and a $\widehat{PSF}$ memory 40. The coefficient calculator 24 provides the coefficient C corresponding to the irradiation condition to an Arithmetic Logic Unit (ALU) 42. The $\widehat{PSF}$ memory 40 stores $\widehat{PSF}$ in the frequency domain and provides the $\widehat{PSF}$ corresponding to the irradiation condition to the ALU 42. The ALU 42 calculates F(ω) as shown in FIG. 13A from the coefficient C and the $\widehat{PSF}$ according to equation (27) and provides F(ω) to an inverse Fourier transformer 44. The inverse Fourier transformer 44 performs the inverse Fourier transformation of F(ω) and provides the result F as shown in FIG. 13B to the convolver 46. The convolver 46 performs the convolution of T' and F in the X-Y domain and produces the scatter distribution T' F or S for the image magnifier 322. The image magnifier converts the size of the image from 64×64 pixels into the original size 512×512 pixels. The subtracter 22 subtracts the 512×512 pixel size of T' F from the image T' to obtain the scatter-glare-free image T-T'** F or P.

Figure 14:
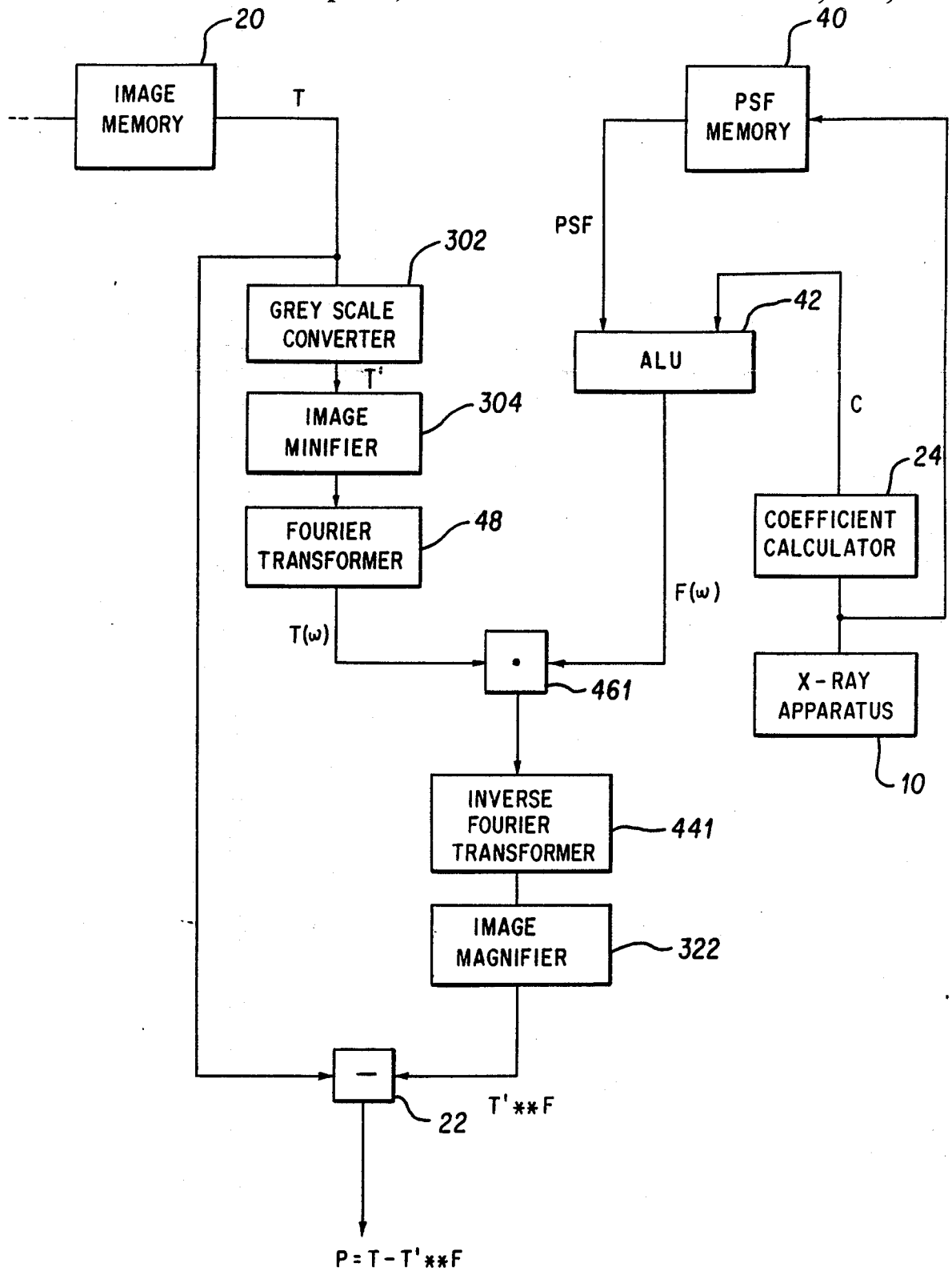
FIG. 14 illustrates a block diagram of a third embodiment of a system which incorporates the teachings of the present invention.

FIG. 14 shows a block diagram of a third embodiment according to the present invention. In the second embodiment as shown in FIG. 12, the convolution of T' and F is performed in the X-Y domain. But, in the third embodiment that convolution is performed in the frequency domain. Accordingly, the third embodiment includes a Fourier transformer 48 for performing a Fourier transformation of the image T' provided from the image minifier 304. The result T(ω) of the Fourier transformation and the output F(ω) provided from the ALU 42 are convoluted by the convolver 461. After that, the convolution result T(ω)·F(ω) is converted into the X-Y domain by an inverse Fourier transformer 441.

Convolution in the frequency domain will be expected to allow for a more rapid calculation.

Additional advantages and modifications will readily occur to those skilled in the art. The invention in its broader aspects is not, therefore, limited to the specific details, representative methods, and illustrative examples shown and described. Accordingly, departures may be made from such details without departing from the spirit or scope of applicant's general inventive concept.

What is claimed is:

1. A system for correcting for scatter radiation S(x,y) in a total radiation distribution T(x,y) of an object to provide a primary radiation distribution P(x,y) of said object, comprising:
   first means for storing a function T(x,y) which represents a distribution of detected radiation passed through the object from a radiation source;
   second means for storing a function $\widehat{PSF}$(x,y) which represents a normalized distribution of detected radiation from said source passed through a mask and a radiation scattering medium;
   means for determining P(x,y)  $\widehat{PSF}$(x,y) as a function of T(x,y) and $\widehat{PSF}$(x,y) and for determining S(x,y) as a function of said P(x,y)  $\widehat{PSF}$(x,y); and
   means for subtracting said scatter radiation S(x,y) from said total radiation distribution T(x,y) to obtain said primary radiation distribution P(x,y).

2. A system according to claim 1, wherein said determining means includes means for solving the following equation:

$$S(x,y) = C \cdot P(x,y) ** \widehat{PSF}(x,y),$$

where C is a constant corresponding to given irradiation conditions under which said total radiation distribution T(x,y) was obtained.

3. The system according to claim 2, wherein said determining means includes:
   means for repeating a calculation of T(x,y) ** ($\widehat{PSF}$(x,y))$^k$ from k=1 to k=a predetermined value Kmax, where k is an integer;
   means for performing the following calculation:

$$I(K\max) = \frac{1}{C+1} T(x,y) ** (\widehat{PSF}(x,y))^{K\max};$$

means for repeating the following calculations until Kmax−l=1:

$$I(K\max-l) = C \cdot T(x,y) ** (\widehat{PSF}(x,y))^{K\max-l} - C \cdot I(K\max-l+1);\text{ and}$$

l=l+1, where l is an integer; and
   means for performing the following calculation:

$$S(x,y) = C \cdot I(1).$$

4. The system according to claim 2, wherein said determining means includes means for performing the following calculation to obtain a convolution kernel F(ω):

$$F(\omega) = C \cdot \widehat{PSF}(\omega)/(1 + C \cdot \widehat{PSF}(\omega)),$$

wherein F(ω) and $\widehat{PSF}$(ω) indicate respective Fourier transformations of F(x,y) and PSF(x,y).

5. The system according to claim 4, wherein said determining means further includes:
   means for obtaining an inverse Fourier transformation F(x,y) of F(ω), and
   means for performing a convolution of F(x,y) and T(x,y) to determine P(x,y) ** $\widehat{PSF}$(x,y).

6. The system according to claim 4, wherein said determining means further includes:
   means for performing a Fourier transformation T(ω) of T(x,y);
   means for performing a convolution T(ω)·F(ω), and
   means for performing an inverse Fourier transformation F(x,y) T(x,y) to determine P(x,y)  $\widehat{PSF}$(x,y).

7. The system according to claim 2, further comprising a grey scale converter for altering the grey scale of T(x,y).

8. The system according to claim 1 further comprising:
   image minifier means, disposed between said first storage means and said determining means, for converting the pixel content of T(x,y) stored in said first storage means into a smaller pixel content; and
   image magnifier means, disposed between said determining means and said subtracting means, for converting the pixel content size of S(x,y) into the same pixel content size as T(x,y).

9. The system according to claim 7, wherein the grey scale converter includes means for altering the grey scale of T(x,y) into T'(x,y) as follows:

$$T'(x,y) = \rho_1 T(x,y) \rho_2,$$

wherein $\rho_1$ and $\rho_2$ are constants satisfying the following equations:

$$T(x,y) = AP(x,y)^n + BP(x,y) + P(x,y), \text{ and}$$

$$T'(x,y) = (AP(x,y)^n + BP(x,y)) \cdot (C+1)/C,$$

wherein n, A and B are constants corresponding to said given irradiations conditions.

10. A system for correcting for scatter radiation $S(x,y)$ in a total radiation distribution $T(x,y)$ of an object under given irradiation conditions to provide a primary radiation distribution $P(x,y)$ of said object under said irradiation conditions, comprising:

first means for storing a function $T(x,y)$ which represents a total distribution of detected radiation passed through the object under said given irradiation conditions;

second means for storing a function $\widehat{PSF}(x,y)$ which represents a normalized distribution of detected radiation passed through a mask and a radiation scattering medium under said given irradiation conditions;

image minifying means for converting a pixel content size of said function $T(x,y)$ into a smaller pixel content;

means for determining $P(x,y)  \widehat{PSF}(x,y)$ as a function of $T(x,y)$ and $\widehat{PSF}(x,y)$ and for determining $S(x,y)$ as a function of $P(x,y)  \widehat{PSF}(x,y)$, wherein $S(x,y)$ represents a distribution of radiation scattered by said object;

image magnifying means for converting a pixel content size of $S(x,y)$ into the same pixel content size as said function $T(x,y)$; and means for subtracting $S(x,y)$ from said image magnifying means from said function $T(x,y)$ to obtain a function $P(x,y)$, which represents a scatter-free distribution of radiation passed through said object under said given irradiation conditions.

11. A method for correcting for scatter radiation $S(x,y)$ in a total radiation distribution $T(x,y)$ of an object to provide a primary radiation distribution $P(x,y)$ of said object, comprising the steps of:

storing a function $T(x,y)$ which represents a distribution of detected radiation passed from a source through the object;

storing a function $\widehat{PSF}(x,y)$ which represents a normalized distribution of detected radiation passed from said source through a mask and a radiation scattering medium;

converting a pixel size of said function $T(x,y)$ into a smaller pixel content;

determining $P(x,y)  \widehat{PSF}(x,y)$ as a function of $T(x,y)$ and $\widehat{PSF}(x,y)$ and determining $S(x,y)$ as a function of said $P(x,y)  \widehat{PSF}(x,y)$, wherein $S(x,y)$ represents a distribution of radiation scattered by said object;

converting a pixel content size of $S(x,y)$ into the same pixel content size as said function $T(x,y)$; and subtracting said function $S(x,y)$ from said function $T(x,y)$ to obtain a function $P(x,y)$, which represents a scatter-free distribution of radiation passed through said object.

12. A method for correcting for scatter radiation $S(x,y)$ in a total radiation distribution $T(x,y)$ of an object under given irradiation conditions to provide a primary radiation distribution $P(x,y)$ of said object, comprising the steps of:

storing a function $T(x,y)$ which represents the total distribution of detected radiation passed through the object from a radiation source under said given irradiation conditions;

storing a function $\widehat{PSF}(x,y)$ which represents a normalized distribution of detected radiation from said source passed through a mask and a radiation scattering medium;

determining $P(x,y)  \widehat{PSF}(x,y)$ as a function of $T(x,y)$ and $\widehat{PSF}(x,y)$ and determining $S(x,y)$ as a function of $P(x,y)  \widehat{PSF}(x,y)$; and subtracting $S(x,y)$ from said function $T(x,y)$ to obtain said function $P(x,y)$.

13. The method according to claim 12, wherein said step of determining comprises the substep of solving the following equation:

$$S(x,y) = C \cdot P(x,y) ** \widehat{PSF}(x,y),$$

where C is a constant corresponding to given irradiation conditions under which said total radiation distribution $T(x,y)$ was obtained.

14. The method according to claim 13, wherein said step of determining further includes the substeps of:

repeating a calculation of $T(x,y) ** (\widehat{PSF}(x,y))^k$ from $k=1$ to $k=a$ predetermined value Kmax, where k is an integer;

performing the following calculations:

$$I(K\text{max}) = \frac{1}{C+1} T(x,y) ** (\widehat{PSF}(x,y))^{K\text{max}};$$

repeating the following calculations until $K\text{max} - 1 = 1$:

$$I(K\text{max}-l) = C \cdot T(x,y) ** (\widehat{PSF}(x,y))^{K\text{max}-l} - C \cdot I(K\text{max}-l+1); \text{ and}$$

$l = l = 1$, where l is an integer; and performing the following calculation:

$$S(x,y) = C \cdot I(1).$$

15. The method according to claim 13, wherein said step of determining includes the substep of performing the following calculation to obtain a convolution kernel $\mathbb{F}(\omega)$:

$$\mathbb{F}(\omega) = C \cdot \mathbb{PSF}(\omega)/(1 + C \cdot \mathbb{PSF}(\omega)),$$

where $\mathbb{F}(\omega)$ and $\widehat{\mathbb{PSF}}(\omega)$ indicate respective Fourier transformations of $F(x,y)$ and $\widehat{PSF}(x,y)$.

16. The method according to claim 15, wherein said step of determining further includes the substeps of:

obtaining an inverse Fourier transformation $F(x,y)$ of $F(\omega)$; and performing a convolution of the function $F(x,y)$ and the function $T(x,y)$ to determine $P(x,y) ** \widehat{PSF}(x,y)$.

17. The method according to claim 15, wherein said step of determining further includes the substeps of:

performing a Fourier transformation $\mathbb{T}(\omega)$ of said function $T(x,y)$;

performing a convolution $\mathbb{T}(\omega)\mathbb{F}(\omega)$; and performing an inverse Fourier transformation $F(x,y)  T(x,y)$ to determine $P(x,y)  \widehat{PSF}(x,y)$.

18. The method according to claim 13, further including the step of altering a grey scale of said function $T(x,y)$.

19. The method according to claim 12, further including the steps of:

converting the pixel content of said function $T(x,y)$ into a smaller pixel content prior to said step of determining; and after said step of determining, converting the pixel content size of S(x,y) into the same pixel size as said function T(x,y).

20. The method according to claim 18, wherein said step of altering includes the substep of changing the grey scale of the function T(x,y) into T'(x,y) as follows:

$$T'(x,y) = \rho_1 \cdot T(x,y)^{\rho_2},$$

wherein $\rho_1$ and $\rho_2$ are constants satisfying the following equations:

$$T(x,y) = AP(x,y)^n + BP(x,y) + P(x,y), \text{ and}$$

$$T'(x,y) = (AP(x,y)^n + BP(x,y)) \cdot (C+1)/C,$$

wherein n, A and B are constants corresponding to said irradiation conditions.

* * * * *

UNITED STATES PATENT AND TRADEMARK OFFICE
CERTIFICATE OF CORRECTION

PATENT NO. : 4,918,713
DATED : April 17, 1990
INVENTOR(S) : MICHITAKA HONDA

It is certified that error appears in the above-identified patent and that said Letters Patent is hereby corrected as shown below:

In the Claims

Claim 4, Column 12, Line 31, change "PSF (x,y)." to --$\widehat{PSF}$ (x,y).--

Claim 12, Column 14, Line 1, change "PSF (x,y)" to --$\widehat{PSF}$ (x,y)--.

Signed and Sealed this

Nineteenth Day of May, 1992

Attest:

DOUGLAS B. COMER

Attesting Officer

Acting Commissioner of Patents and Trademarks